Figure 1:
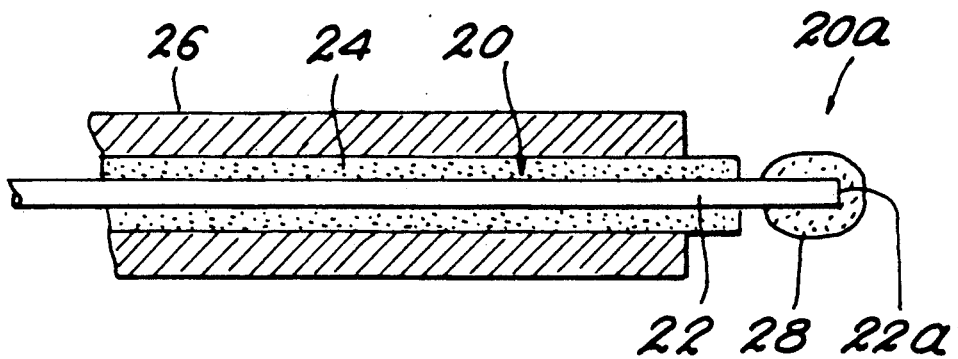

United States Patent [19]

Sebille et al.

[11] Patent Number: 5,028,395
[45] Date of Patent: Jul. 2, 1991

[54] ACTIVE CHEMICAL SENSOR WITH OPTICAL FIBER AND ITS PRODUCTION PROCESS

[75] Inventors: Bernard Sebille, Clamart; Bruno Biatry, Paris; Gilbert Boisde, Bures sur Yvette, all of France

[73] Assignees: Commissariat a l'Energie Atomique, Paris; Photonetics, Marly-le-Roi, both of France

[21] Appl. No.: 552,795

[22] Filed: Jul. 16, 1990

[30] Foreign Application Priority Data

Jul. 20, 1989 [FR] France .................. 89 09786

[51] Int. Cl.⁵ .................. G01N 21/00; A61B 5/00; C09B 69/10; G02B 6/16
[52] U.S. Cl. .................. 422/82.06; 422/82.07; 422/68.1; 128/633; 128/634; 128/636; 436/172; 350/96.29; 350/96.34; 356/402; 356/432; 8/541; 8/543; 8/647
[58] Field of Search .................. 422/82.06, 82.07; 128/633, 634, 636; 350/96.34, 96.10, 96.29; 8/541, 542, 543

[56] References Cited

U.S. PATENT DOCUMENTS

| | | | |
|---|---|---|---|
| 4,194,877 | 3/1980 | Peterson .................. | 128/634 |
| 4,200,110 | 4/1980 | Peterson et al. .................. | 128/634 |
| 4,391,797 | 7/1983 | Folkman et al. .................. | 424/425 |
| 4,560,248 | 12/1985 | Cramp et al. .................. | 128/633 |
| 4,663,272 | 5/1987 | Nakamura .................. | 430/542 |
| 4,803,049 | 2/1989 | Hirschfeld et al. .................. | 422/58 |
| 4,906,249 | 3/1990 | Fogt et al. .................. | 128/634 |

FOREIGN PATENT DOCUMENTS

| | | |
|---|---|---|
| 384891 | 1/1988 | Austria . |
| 0072627 | 2/1983 | European Pat. Off.. |
| 0263693 | 4/1988 | European Pat. Off. .................. 128/633 |
| WO88/05533 | 7/1988 | PCT Int'l Appl. . |

Primary Examiner—Robert J. Warden
Assistant Examiner—Theresa A. Trembley
Attorney, Agent, or Firm—Pearne, Gordon, McCoy & Granger

[57] ABSTRACT

Active chemical sensor with optical fiber and its production process.

The chemical sensor according to the invention makes it possible to measure a given quantity or magnitude of a fluid. It has a chemical reagent suitable for the measurement and for reacting with the fluid, a support means (20a, 28) for the reagent and a single optical fiber (20) for supplying light to the reagent and recovering the light reflected by the reagent, said sensor being characterized in that the support means incorporates a vinyl imidazole polymer or copolymer film (28) in which the reagent is immobilized, said polymer being in particular directly grafted on to one of the ends (20a) of the optical fiber (20).

13 Claims, 3 Drawing Sheets

ACTIVE CHEMICAL SENSOR WITH OPTICAL FIBER AND ITS PRODUCTION PROCESS

DESCRIPTION

The present invention relates to an active chemical sensor with optical fiber for the remote measurement of a given magnitude or quantity of a generally fluid medium. It is more particularly used in the nuclear and industrial fields for checking chemical processes, the environment for checking buried nuclear waste, medical and biological analysis and in the agroalimentary industry e.g. using microorganisms.

This sensor makes it possible to measure the concentration of chemical species in fluid media and in particular cations or anions, as well as the measurement of the pH of liquid solutions, or the measurement of the partial pressure of gases such as oxygen or carbon dioxide gas in gaseous mixtures or liquids.

More specifically, the invention makes it possible to carry out pH measurements between 3 and 9 and in particular the pH of systems having substantially constant ionic strength such as blood, blood plasma, sea water and pH-values close to neutrality, as well as the measurement of the partial pressure of $CO_2$ in such media.

The sensor according to the invention permits remote measurements, over several kilometers if necessary, using the standard methods of optical absorptiometry (photometry, reflectance, spectrophotometry) and luminance (chemiluminescence, fluorescence and phosphorescence).

The invention can also be used for producing physical sensors making it possible to measure the temperature by triboluminescence.

The present invention solely relates to the sensitive part of a chemical sensor and not to the measuring apparatus or signal processing system associated therewith. This sensitive part is known as the "opto" or "optode".

In addition, the sensor according to the invention belongs to the category of so-called active optodes, as opposed to so-called passive optodes.

Passive optodes have one or more optical fibers used solely as a light guide with a view to studying an effect (absorption, fluorescence) in a fluid medium. Active optodes have one or more fibers, whose end supports an immobilized chemical reagent which, in contact with the fluid medium to be studied, intereacts with light from the fiber or fibers. The study of the light resulting from said interaction makes it possible to obtain the results of the measurement.

In particular, said reagent is a substance, whose color varies under the effect of the studied quantity of the medium and it is possible to observe this coloring variation in absorption or fluorescence as a function of the chemical reagent-medium reaction used.

When the optical properties of the actual fibers are modified, particularly by the chemical reaction of a component on the fibers or on the end thereof, the corresponding optode is said to be active intrinsic. In such an optode, evanescent waves are used for the measurement.

When the optical properties of the optical fibers are not modified, the corresponding optode is said to be active extrinsic.

For more information on optodes and their operation, reference can be made to the publication by G. BOISDE and J. J. PEREZ "Une nouvelle génération de capteurs : les optodes", La Vie des Sciences reports, general series, vol.5, no.5, pp.303–332, 1988.

Passive optodes require the appropriate dilution of a chemical reagent in a liquid medium, so that the use thereof involves a large amount of time and the production of sometimes noxious effluents (industrial and nuclear fields), which it is necessary to treat and/or store. In addition, their applications are limited.

In addition, a sensor of the active extrinsic optode type with optical fibers is known for measuring the pH or the partial pressure of $CO_2$ in a liquid medium, cf. FR-A-2 613 074 filed in the name of the present Applicant. This sensor has an emitting optical fiber used for reflecting the light in the direction of a microsphere to which is fixed the chemical reagent and a receiving optical fiber used for recovering the light from the reagent.

This sensor has a certain number of advantages such as a good stability and long life, as well as easy sterilization permitting it to be reused a considerable number of times. However, unfortunately the interaction between the optical fibers and the reagent immobilized in the microsphere is not sufficiently reproducible and the reaction kinetics between the medium to be studied and the reagent is not adequately fast in neutral media. Thus, the sensor is only usable in media having an acid pH ($<3$) or basic pH ($>9$). Therefore it does not permit analysis in a neutral medium and in particular the measurement of the neutral pH.

Another sensor of the active extrinsic optode type is disclosed in the article by F. V. Bright et al "A new ion sensor based on Fiberoptics", Talanta, vol.35, no.2, 1988, p.113–118. This sensor makes use of a NAFION membrane as the support for a fluorophoric substance mounted at the end of two juxtaposed optical fibers, one emitting and the other receiving. This sensor is used for measuring the concentration of a large number of chemical species.

The known optodes of the active extrinsic type suffer from the disadvantage of having large dimensions, which limits the miniaturization thereof and increases the response time thereof.

A sensor of the active intrinsic optode type for measuring $CO_2$ is described by C. MUNKHOLM and D. R. WALT in the article "A fiber-optic 2, 1988, pp.109–112. It has a polymer of the acrylamide or hydroxyethyl methacrylate type, grafted on to the sensitive end of a single optical fiber, in which is immobilized a fluorophoric substance by copolymerization or adsorption, as well as an ion exchange membrane covering the polymer. The presence of said membrane increases the response time of the sensor and is prejudicial to its sterilization.

Another sensor of the active intrinsic optode type for immunoassays is described in "Fiber-optic time resolved fluorimetry for immuno-assays" by R. D. PETREA et al, Talanta, vol.35, no.2, 1988, pp.139–144. It has a polymer of the polypropylene type in which is immobilized a biological reagent by covalent bonding.

Apart from their inherent disadvantages, these active intrinsic optodes are only usable for a particular measuring technique. Moreover, they are incompatible with the disposable or disconnectable optode principle with a view to changing the sensitive zone or the optode principle using several coloring agents or dyes simultaneously.

The invention relates to a fiber optic or optical fiber chemical sensor of the active chemical optode type making it possible to obviate the disadvantages referred to hereinbefore. This sensor can be used in all optical measurement procedures such as absorption, reflectance, luminance or measurement by evanescent wave and is able to supply a response in a very short period of time (less than 30 seconds and even less than 10 seconds). Moreover, said sensor can be used in a wide pH range between 3 and 9 and in particular makes it possible to measure a neutral pH.

More specifically, the present invention relates to an active chemical sensor with optical fiber for measuring a given quantity or magnitude of a fluid having a chemical reagent appropriate for the measurement and able to react with the fluid, a support means for the said reagent and a single optical fiber for supplying light to the reagent and recovering the light reflected by the reagent, the sensor being characterized in that the support means has a vinyl imidazole polymer or copolymer film in which the reagent is immobilized.

The sensor according to the invention is usable in all optical measurement methods. Moreover, it has a fast response time. It is biocompatible and sterilizable, whilst the sensor has no membrane, so that its response time is improved. Finally, it is usable in a pH range between 3 and 9.

The thinner the polymer or copolymer film, the faster the sensor response time, the film thickness being 3 to 100 micrometers.

The polyvinyl imidazole used in the invention is a known polymer having a recurring unit represented by one or other of the formulas I and II given in appendix I in which $R_1$ represents a straight or branched chain alkyl group with 1 to 4 carbon atoms, e.g. a methyl, ethyl, or n-propyl group, or a group of formula —$CH_2$-$CHOH$-$CH_2X$, X being a hydrogen atom, a halogen atom such as chlorine, bromine or iodine, a hydroxy group or a hydroxyalkyl chain with 1 to 4 carbon atoms and $R_2$ represents a hydrogen atom or a methyl group.

It is possible to use a polyvinyl imidazole with a molecular weight e.g. between 5000 and 200 000.

The monomer copolymerizable with the vinyl imidazole can be a derivative with ethylene unsaturation of formula $CH_2=CR_3R_4$, in which $R_3$ represents a hydrogen atom or a methyl group and $R_4$ represents a lower alkoxy group with 1 to 3 carbon atoms, an amino, dimethylamino, cyano, n-pyrrolidone and in particular N-pyrrolid-2-one group, a group of formula —$COOR_5$ in which $R_5$ is a hydrogen atom or a methyl, ethyl, epoxy ethyl, 2,3-epoxy profile or hydroxyalkyl group with 1 to 3 carbon atoms, a —$CONR_6R_7$ group in which $R_6$ and $R_7$, which can be the same or different, represent a halogen atom, an alkyl group with 1 to 3 carbon atoms, a hydroxyalkyl group with 1 to 4 carbon atoms and in particular a tri(hydroxymethyl)-methyl group, or a silane radical of formula —$SiX_3$, in which X is a hydrogen or halogen atom (e.g. chlorine or bromine) or an alkoxy group with 1 to 4 carbon atoms, an acetoxy group or a phenoxy group.

The copolymerizable monomer can more particularly be chosen from among acrylamide, N-vinyl pyrrolidone, vinyl trimethoxysilane, vinyl triacetoxysilane, vinyl trichlorosilane, ethylene glycol acrylate, glycidyl acrylate and trihydroxymethyl acrylamide. The polymerization of the comonomers takes place by conventional methods. Preference is given to the use of a poly(vinyl imidazole) polymer.

Thus, poly (vinyl imidazole), abbreviated hereinafter to PVI, has the advantage of being compatible with the biological media such as blood and blood plasma, unlike the polymers used hitherto in the aforementioned optodes and certain copolymers according to the invention.

Preferably the optical fiber constitutes an essential part of the support for the chemical reagent. This makes it possible to miniaturize the sensor with fibers between 200 microns and max 1 mm and as a result it is possible to obtain a directly integrated arrangement compatible with a long distance fiber transmission. Preferably, the polymer containing the reagent is directly grafted on to one end of the optical fiber.

The optical fiber usable in the invention can be constituted by plastic fibers and in particular polymethacrylate, methyl or polystyrene fibers, borosilicate glass fibers, quartz fibers or silica fibers.

The chemical reagent can be fixed to the polymer by covalent bonds or ionic bonds or by adsorption. The chemical reagents are chromophores, which can be color indicators, luminescent chemical components (luminophores) or fluorescent chemical components (fluorophores).

In order to increase the pH use range for the sensor, the chemical reagent can be constituted by a mixture of chromaphores.

In the particular application to the measurement of the pH or the $CO_2$ pressure of an aqueous solution, use is made of chromophores of the color indicator type having a sulphonic acid function.

The invention also relates to a process for producing the aforementioned sensor.

In particular, said process makes it possible to produce an active chemical sensor having a vinyl imidazole polymer or copolymer film grafted on to the end of an optical fiber having silanol groups and containing a chemical reagent which is appropriate for the measurement.

This process comprises the following stages:

a) polymerizing or copolymerizing the vinyl imidazole, b) activating the end of the fibre in order to release the silanol groups, c) reacting the activated silanol groups with an organosilane having a function able to react with the vinyl imidazole polymer or copolymer, d) reacting said function in order to graft the polymer or copolymer to the optical fiber, e) crosslink the polymer or copolymer, f) alkylating or benzylating the non-quaternized imidazole units and g) immobilizing the chemical reagent in the polymer or copolymer.

The organosilane usable in the invention in particular has an epoxide, chloride, amine, vinyl or methacryloyl function and the carbon chain has 1 to 20 carbon atoms.

Examples of organosilanes are 3-glycidoxypropyltrimethoxy or triethoxy silane, aminopropyl triethoxysilane, chloropropyl triethoxysilane, triethoxysilyl propane thiol, N-(2-aminoethyl)-3-aminopropyl trimethoxysilane, glycidyloxypropyl trimethoxy silane, triacetoxy vinyl silane or methacryloxypropyl trimethoxy silane.

The order of the stages of this process can be modified. In particular, stage a) of producing the basic polymer or copolymer can take place before or after stages b) and c) relative to the prior preparation of the optical fiber. In addition, the impregnation of the polymer or copolymer by the chemical reagent can take place just after the crosslinking stage e) or during the use of the sensor.

Advantageously, the crosslinking stage takes place in the presence of a polyfunctional and in particular bifunctional compound. In addition, the crosslinking can be carried out by a radiochemical process.

The invention is described in greater detail herinafter relative to non-limitative embodiments and the attached drawings, wherein show:

FIG. 1 Diagrammatically a first embodiment of a sensor according to the invention.

Figure 2:
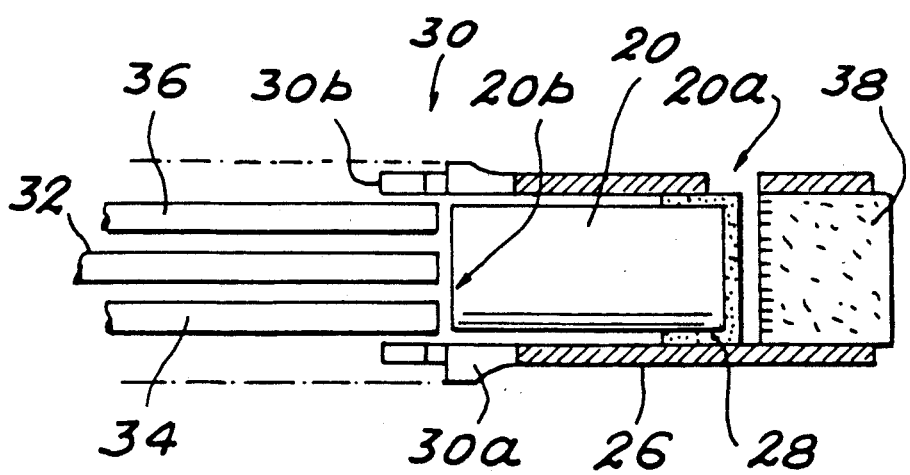

FIG. 2 Diagrammatically a second embodiment of a sensor according to the invention.

Figure 3:
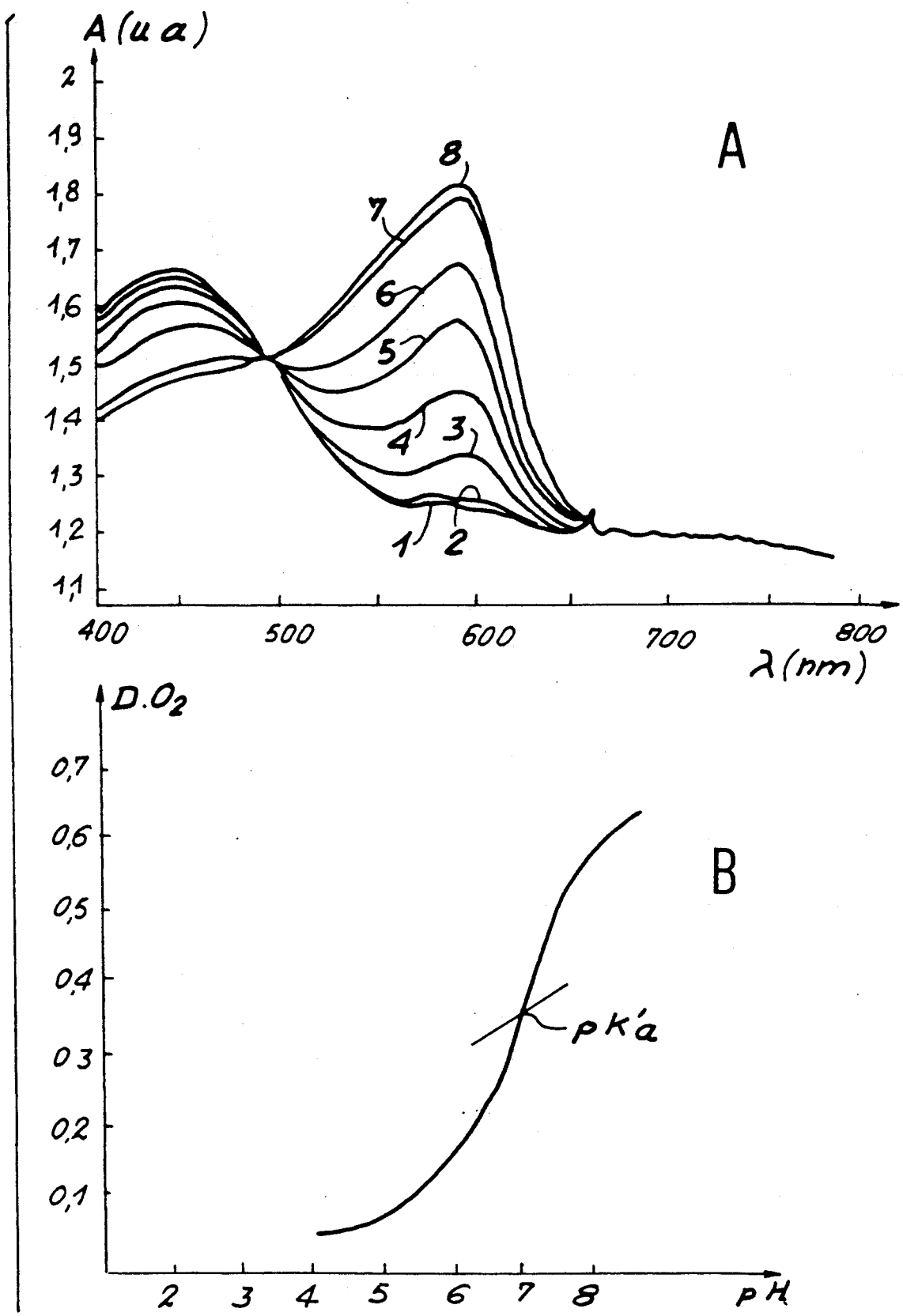

FIG. 3 The absorption spectrum of the sensor of FIG. 1 with tetrabromophenol sulphone phthalein as the chemical reagent; part (A) of FIG. 3 giving the absorption (A) in arbitrary units (a.u) as a function of the wavelenth ($\lambda$) expressed in nanometers and part B of FIG. 3 the optical density (O.D.) as a function of the pH.

Figure 4:
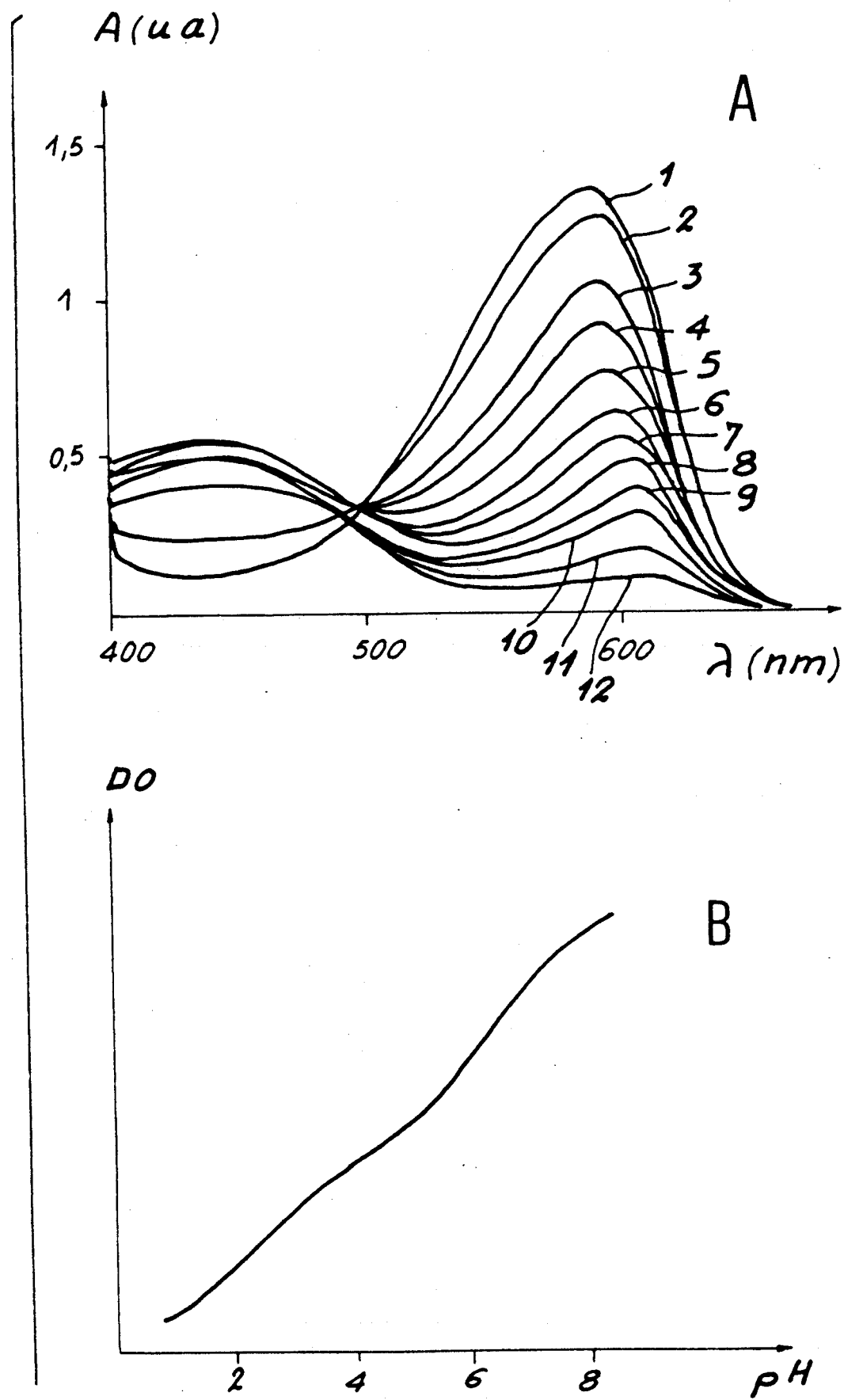

FIG. 4 The absorption spectrum of the sensor of FIG. 1 with a mixture of color indicators as the chemical reagent; part A of FIG. 4 giving the absorbtivity in arbitrary units as a function of the wavelength in nm and part B the optical density as a function of the pH.

FIG. 1 shows an active chemical sensor or optode according to the invention. This sensor has an optical fiber 20 with a silica core 22 covered by an optical sheath 24 made from a plastics material and in particular silicone or a chlorine or fluorine-containing polymer. This type of fiber has the advantage of being easily bared. The fiber diameter is approximately 1 mm. A mechanical sheath 26 of a biocompatible material such as stainless steel protects the complete optical fiber.

The sensitive end 20a of the optical fiber is bared so as to expose approximately 1 cm of core. The bare core end 22a is optically polished. On to said core end 22a is grafted an approximately 5 micrometer thick vinyl imidazole polymer or copolymer film 28, in which is immobilized one or more chromophores and in particular fluorophores or color indicators.

The other end of the optical fiber 20 is connected to a known data processing system, as described in FR-A-2 613 074 and in the articles by F. V. BRIGHT or R. D. PETREA referred to hereinbefore. The optical fiber can have a length of several dozen meters.

The sensor shown in FIG. 1 is essentially intended to operate in absorptivity and fluorescence. For an analysis of a fluid medium in reflectance, preference is given to the use of the sensors shown in FIG. 2. The latter essentially differs from that shown in FIG. 1 by the fact that the end 20b of the optical fiber 20 (opposite to the sensitive end 20a) is equipped with a connector 30 making it possible to connect the optical fiber 20 of the sensor e.g. to three other groups of optical fibers 32, 34 and 36 arranged in ring-like manner and which can have a length of 100 meters, the optical fiber 20 of the sensor only having a length of 4 to 20 cm. The fibers 32 can be used for supplying light to the optical fiber 20 and fibers 34 and 36 can be used for recovering the light from the coloring agent immobilized in the polymer film 28, when it is illuminated.

The connector 30 can be dismantled, which makes it possible to change or replace the optode as often as necessary. The connector part 30a can be joined to the optical fiber 20 by bonding. In the same way, connector part 30b can be joined to the optical fibers 32 to 36 by bonding.

In order to amplify the light signal from the coloring agent immobilized in the polymer film 28, it is possible to position a reflector 38 in front of the sensitive end 20a. Said reflector 38 is fixed by bonding in an extension of the mechanical sheath 26.

FIGS. 3 and 4 show the absorption spectra of the sensor according to the invention shown in FIG. 1, as a pH-meter, in the case of tetrabromophenol sulphone phthalein, designated TBPSP as an abbreviation and used respectively alone or mixed with chlorophenol red. The spectrum of FIG. 3 corresponds to 0.8% by weight TBPSP in a solvent containing 80% by volume of methanol and 20% by volume of water and the spectrum of FIG. 4 corresponds to 0.1% by weight of TBPSP+0.1% by weight of chlorophenol red in the same solvent. The pka of TBPSP is 6.95.

Curves A of FIGS. 3 and 4 give the absorptivity as a function of the wavelength and curves B thereof the optical density as a function of the pH.

Curves 1 to 8 in part A of FIG. 3 correspond to pH-values from 3.3 to 8.2 and curves 1 to 12 in FIG. 4 to pH-values from 2 to 9.

It can be clearly gathered from these curves that the sensor or optode according to the invention can be used for measuring pH-values between 3 and 9. It can also be gathered from curve B of FIG. 4 that an appropriate mixture of color indicators can lead to a substantially linear variation of the optical density as a function of the pH.

The production of the sensor or optode according to the invention will now be described.

Stage (a): Production of the poly(vinyl imidazole).

The first stage of the production process for the sensor according to the invention consists of polymerizing the vinyl imidazole of formulas I or II given in appendix I with the aid of a radical initiator representing 0.5 to 2 molar % based on the monomer. This polymerization is carried out hot at between 40° and 100° C. under an inert atmosphere (rare gas or nitrogen).

EXAMPLE

Into 100 millimeters of pure methanol are introduced 16.30 millimeters (i.e. approximately 16.9 g or 0.18 moles) of freshly distilled vinyl imidazole. After degassing with nitrogen, a reaction initiator is added, namely 236 mg (i.e. $1.44 \cdot 10^{-3}$ moles) of azobis-isobutyronitrile, which corresponds to 0.8 molar % of initiator based on the monomer. The mixture is heated to 60° C. for 48 hours. The polymer is then precipitated in acetone. The powder obtained is dried in vacuo for 24 hours and essentially contains poly(vinyl imidazole) PVI.

The following stages of the process consist of preparing the optical fiber of the sensor in order to permit the grafting of PVI. To this end an optical fiber having a silica core 22 and a plastic optical sheath 24 is freed from its optical sheath at one of its ends 20a over a distance of approximately 1 cm. This bare end is then polished and activated.

Stage b): Activation of the optical fiber.

The activation consists of cleaning the end of the fiber by an acid treatment and a "surface release" of free silanol from the fiber, corresponding to chemical reaction (III) given in appendix I.

EXAMPLE

This operation of activating the end of the fiber is carried out in a 50:50 mixture of nitric acid and sulphuric acid in concentrated form for 30 minutes and at ambient temperature. The fibers are then washed several times in distilled water and then acetone. The treatment is followed by drying in the oven at 90° C.

Stage c): Reaction of the activated silanol group.

This stage consists of reacting the silanol groups with an organosilane having a function able to subsequently react with the poly(vinyl imidazole). It is e.g. possible to use an organosilane already having an epoxide function or to operate in two phases, namely firstly the incorporation of the organosilane, followed by a reaction with a molecule having an epoxide function in accordance with standard reactions (e.g. acid-alcohol).

This gives a junction indicated at (IV) in appendix I. Thus, this stage consists of grafting the fiber to an organosilane with an epoxide function.

EXAMPLE

This grafting operation can be carried out by immersing the fiber end in a 3-glycidoxypropyl trimethoxysilane solution which has been freshly distilled, 50% diluted in anhydrous toluene and heated to 90° C. in an inert atmosphere (particularly nitrogen).

It is also possible to use 3-glyciloxypropyl triethoxysilane. After 24 hours the fiber is washed several times in toluene to remove the excess reagent and then in dichloromethane. It is then placed for 24 hours in an oven at 90° to 95° C. in order to dry it. The silanization reaction is given in appendix I by reaction (V).

Stage d): Grafting the polymer.

The following stage of the process consists of grafting the PVI on the activated optical fiber. The epoxide function grafted on to the optical fiber serves as a coupling agent with the poly(vinyl imidazole) according to reaction (VI) given in appendix II. Certain imidazole groups may not be directly linked to the optical fiber.

EXAMPLE

Reaction (VI) can be obtained by dissolving PVI in propanol at a rate of 50 g/l (5% by weight). 1.2 ml of this solution is then diluted in 1.8 ml of propanol and is then brough to 65° C., accompanied by slight stirring. The end of the activated fiber is vertically immersed in it for 60 minutes. However, it is necessary to create intramolecular and intermolecular bonds between the PH chains in order to improve its strength.

Stage e): Crosslinking the polymer.

For this purpose the PVI is crosslinked with a bifunctional reagent having in particular two electrophilic functions, namely chloride, such as e.g. $\alpha$-$\alpha'$-paradichlorooxylene, two epoxide functions or a chloride function and an epoxide function, such as e.g. epichlorohydrin. In the case of epichlorohydrin, the cross-linking process is that given by reaction (VII) in appendix II.

EXAMPLE

This crosslinking stage is carried out with 0.2 ml of epichlorohydrin ($2.44.10^{-3}$ moles), the temperature being kept at 65° C. for 45 minutes, accompanied by stirring. However, this stage does not lead to a total "quaternization" of the imidazole units for steric hindrance reasons.

It is also advantageous to add thereto an alkylation or benzylation stage with respect to the non-quaternized imidazole units in order to form a continuous, rigid polymer film.

Stage f): Alkylation of the non-quaternized units.

For this purpose, an alkylation reaction is carried out with 8% by volume methyl iodide, at 60° to 70° C. and for 60 minutes. This is followed by washing with propanol and drying at 80° C. The reaction with methyl iodide is indicated at (VIII) in appendix II.

the methyl iodide can be replaced by alkyl chlorides or bromides with 1 to 10 carbon atoms, or benzyl chlorides or bromides.

Following said alkylation, the optical fiber is dried in air for a few minutes and then left in the oven overnight at 90° C. It is then ready for impregnation by the chemical reagent, which can be carried out several days afterwards.

Stage g): Immobilization of the chemical reagent.

The final stage of the process consists of immobilizing the chemical reagent in grafted and crosslinked polymer. The immobilization takes particular advantage of the presence of a positive charge on the imidazole unit for fixing chemical reagents having an electronegative function and in particular a sulphonic acid function ($-SO_3H$).

When the chemical reagent is a color indicator intended in particular for measuring the pH of a liquid or for measuring the $CO_2$ pressure in a liquid, use is made of a sulphone phthalein such as chlorophenol red, bromophenol red, bromophenol blue, bromocresol green, bromothymol blue, 3,4,6,8-tetrabromophenol sulphone phthalein and mixtures thereof. these color indicators have the advantage of a pka between 3 and 9.

Preference is given to the use of tetrabromophenol sulphone phthalein as a result of its absorption spectrum being in the center of the visible range (592 nm), whilst its pka is close to 7.

The immobilization of the chemical reagent on the polymer is relatively simple.

EXAMPLE

Immobilization takes place by contact with a methanolic solution of coloring agents (0.1% by weight). The active end of the sensor is immersed for between 30 seconds and 60 minutes in a beaker containing the coloring agent solution in an 80:20 methanol-water mixture, accompanied by stirring. The sensor is then rinsed with water for a few minutes and is ready for use. Methanol can be replaced by ethanol.

The impregnation time is determined by the desired quantities of the sensor (maximum absorption value, reaction speed) and the type of color indicator used.

For an operation in fluorescence, the coloring agent or agents are replaced by a fluorophore such as salts of fluoresceine. rhodamine, etc.

We claim:

1. Active chemical sensor with optical fiber for measuring a determined physical quantity of fluid, comprising a chemical reagent appropriate for the measurement and able to react with the fluid, a support means (20a, 28) for the reagent and a single optical fiber (20) for supplying light to the reagent and for recovering the light reflected by the reagent, the sensor being characterized in that the support means has a crosslinked vinyl imidazole polymer or copolymer film (28) in which the reagent is immobilized, said film being bonded directly on one end (20a) of the optical fiber (20).

2. Sensor according to claim 1, characterized in that the optical fiber has a silica core (22).

3. Sensor according to claim 1, characterized in that the reagent is essentially fixed by ionic bonds to the polymer.

4. Sensor according to claim 1, characterized in that the chemical reagent is constituted by a mixture of chromophores.

5. Sensor according to claim 1, characterized in that a protective envelope (26) is provided for protecting the polymer containing the reagent.

6. Sensor according to claim 1, characterized in that the sensor is a dismantable sensor and that the optical fiber is provided on the end (20b) opposite that facing the reagent with an optical connector (30) for mounting on at least one other optical fiber (32, 34, 36).

7. Sensor according to claim 1 for measuring the pH of a liquid, characterized in that the chemical reagent contains at least one chromophore having a sulphonic acid function.

8. Sensor according to claim 1, characterized in that the chemical reagent is chosen from the group consisting of chlorophenol red, bromophenol red, bromophenol blue, bromocresol green, bromothymol blue, 3,4,6,8-tetrabromophenol sulphone phthalein and mixtures thereof.

9. Process for the production of a chemical sensor for measuring a determined physical quantity of fluid having a vinyl imidazole polymer or copolymer film (28) bounded directly on to a end of an optical fiber (20a) having silanol groups and containing a chemical reagent suitable for the measurement and able to react with the fluid, characterized in that it comprises the following stages:
a) polymerizing or copolymerizing the vinyl imidazole,
b) activating the end of the fiber (20a) for releasing its silanol groups,
c) reacting the activated silanol groups with an organosilane having a function able to react with the vinyl imidazole polymer or copolymer,
d) reacting said function in order to graft the polymer or copolymer to the optical fiber,
e) crosslinking the polymer or copolymer,
f) alkylating or benzylating the non-quaternized imidazole units and
g) immobilizing the chemical reagent in the polymer or copolymer.

10. Process according to claim 9, characterized in that the function of the organosilane able to react with the vinyl imidazole is the epoxide function.

11. Process according to claim 9, characterized in that the crosslinking stage (e) takes place in the presence of a polyfunctional chemical compound.

12. Process according to claim 9, characterized in that the crosslinking stage (e) takes place with the aid of epichlorohydrin.

13. Sensor according to claim 7, characterized in that the chemical reagent is chosen from the group consisting of chlorophenol red, bromophenol red, bromophenol blue, bromocresol green, bromothymol blue, 3,4,6,8-tetrabromophenol sulphone phthalein and mixtures thereof.

* * * * *